(12) United States Patent
Geall

(10) Patent No.: US 7,521,187 B2
(45) Date of Patent: Apr. 21, 2009

(54) METHOD FOR FREEZE-DRYING NUCLEIC ACID/BLOCK COPOLYMER/CATIONIC SURFACTANT COMPLEXES

(75) Inventor: Andrew Geall, Del Mar, CA (US)

(73) Assignee: Vical Incorporated, San Diego, CA (US)

( * ) Notice: Subject to any disclaimer, the term of this patent is extended or adjusted under 35 U.S.C. 154(b) by 565 days.

(21) Appl. No.: 10/725,009

(22) Filed: Dec. 2, 2003

(65) Prior Publication Data

US 2004/0157789 A1 Aug. 12, 2004

Related U.S. Application Data

(60) Provisional application No. 60/435,273, filed on Dec. 23, 2002.

(51) Int. Cl.
| | |
|---|---|
| C12Q 1/00 | (2006.01) |
| C12Q 1/68 | (2006.01) |
| C12P 19/34 | (2006.01) |
| C12N 13/00 | (2006.01) |
| A61K 36/14 | (2006.01) |

(52) U.S. Cl. .................. 435/6; 424/1.11; 424/1.13; 435/4; 435/40.5; 435/91.1; 435/173.9

(58) Field of Classification Search ............ 106/31.59; 424/1.11, 1.21, 70.11, 70.19, 70.27, 78.08, 424/178.1, 184.1, 278.1; 430/115; 435/112; 570/475; 576/191; 525/198, 90; 530/421
See application file for complete search history.

(56) References Cited

U.S. PATENT DOCUMENTS

| | | | |
|---|---|---|---|
| 5,264,618 A | 11/1993 | Felgner et al. | |
| 5,459,127 A * | 10/1995 | Felgner et al. | 514/7 |
| 5,567,859 A | 10/1996 | Emanuele et al. | |
| 5,656,611 A | 8/1997 | Kabanov et al. | |
| 5,674,911 A | 10/1997 | Emanuele et al. | |
| 5,691,387 A | 11/1997 | Emanuele et al. | |
| 5,696,298 A | 12/1997 | Emanuele et al. | |
| 5,703,055 A | 12/1997 | Felgner et al. | |
| 5,709,879 A | 1/1998 | Barchfeld et al. | |
| 5,811,088 A * | 9/1998 | Hunter et al. | 424/78.08 |

(Continued)

FOREIGN PATENT DOCUMENTS

WO  WO 96/04392 A2  2/1996

(Continued)

OTHER PUBLICATIONS

Corveleyn, S. and Remon, J.-P., "Maltodextrins as Lyoprotectants in the Lyophilization of a Model Protein, LDH," *Pharm. Res.* 13:146-150, Plenum Publishing Corporation (1996).

Kim, A.I., et al., "The Physical State of Mannitol after Freeze-Drying: Effects of Mannitol Concentration, Freezing Rate, and a Noncrystallizing Cosolute," *J. Pharm. Sci.* 87:931-935, American Chemical Society (1998).

(Continued)

*Primary Examiner*—Robert B Mondesi
*Assistant Examiner*—J. Hines
(74) *Attorney, Agent, or Firm*—DLP Piper LLP (US)

(57) ABSTRACT

This invention relates generally to the freeze-drying of formulations comprising a polynucleotide, a block copolymer and a cationic surfactant. In the presence of a cryoprotectant or bulking agent, a formulation can be freeze-dried, whereby upon reconstitution of the dried formulation, the microparticles maintain their optimal size and aggregation or fusion is avoided.

29 Claims, 2 Drawing Sheets

U.S. PATENT DOCUMENTS

Figure 1A:
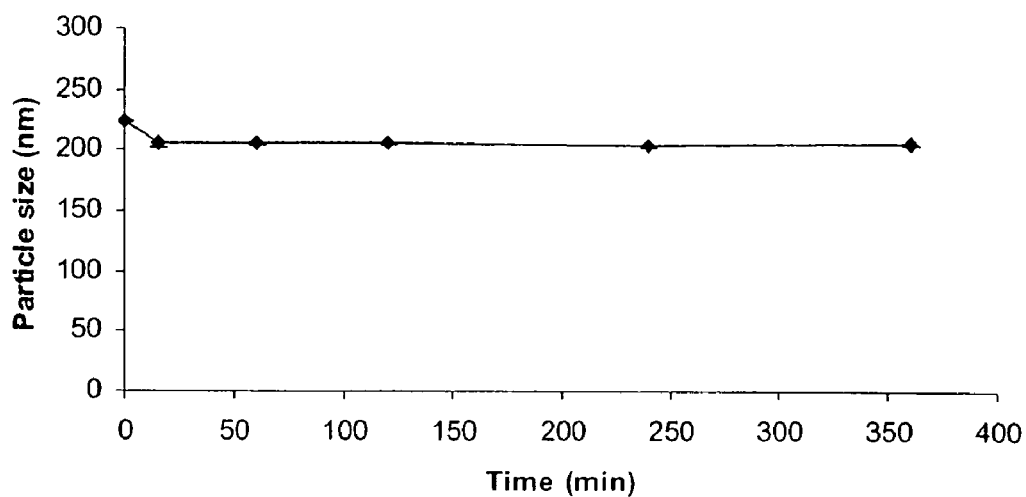

| | | | |
|---|---|---|---|
| 5,817,334 A | 10/1998 | Schmidt et al. | |
| 5,824,322 A * | 10/1998 | Balasubramanian | 424/280.1 |
| 5,990,241 A * | 11/1999 | Emanuele et al. | 525/88 |
| 5,994,314 A | 11/1999 | Eljamal et al. | |
| 5,994,317 A | 11/1999 | Wheeler | |
| RE36,665 E | 4/2000 | Emanuele et al. | |
| 6,147,055 A | 11/2000 | Hobart et al. | |
| 6,248,363 B1 * | 6/2001 | Patel et al. | 424/497 |
| 6,251,599 B1 * | 6/2001 | Chen et al. | 435/6 |
| 6,359,054 B1 | 3/2002 | Lemieux et al. | |
| 6,399,588 B1 | 6/2002 | Hobart et al. | |
| 6,482,518 B1 | 11/2002 | Short et al. | |
| 6,586,409 B1 | 7/2003 | Wheeler | |
| 6,670,332 B1 | 12/2003 | Wheeler | |
| 6,867,195 B1 | 3/2005 | Felgner et al. | |
| 6,875,748 B2 | 4/2005 | Manthorpe et al. | |
| 2002/0019358 A1 | 2/2002 | Manthorpe et al. | |
| 2003/0032615 A1 | 2/2003 | Felgner et al. | |
| 2003/0186913 A1 | 10/2003 | Wolff et al. | |
| 2003/0191082 A1 | 10/2003 | Wheeler | |
| 2003/0203863 A1 | 10/2003 | Hobart et al. | |
| 2004/0157789 A1 | 8/2004 | Geall | |
| 2004/0162256 A1 | 8/2004 | Geall et al. | |
| 2004/0171572 A1 | 9/2004 | Wheeler | |
| 2004/0209241 A1 | 10/2004 | Hermanson et al. | |

FOREIGN PATENT DOCUMENTS

| | | | |
|---|---|---|---|
| WO | WO 96/04932 A1 | | 2/1996 |
| WO | WO 97/40839 | * | 1/1997 |
| WO | WO 97/40839 A1 | | 11/1997 |
| WO | WO 99/06055 A1 | | 2/1999 |
| WO | WO 99/21591 | * | 5/1999 |
| WO | WO 99/21591 A1 | | 5/1999 |
| WO | WO 00/57917 A2 | | 10/2000 |
| WO | WO 01/65911 A2 | | 9/2001 |
| WO | WO 02/00844 | * | 1/2002 |
| WO | WO 02/00844 A2 | | 1/2002 |
| WO | WO 2004/060059 | | 7/2004 |
| WO | WO 2004/060363 | | 7/2004 |

OTHER PUBLICATIONS

Martini, A., et al., "Use of Subambient Differential Scanning Calorimetry to Monitor the Frozen-State Behavior of Blends of Excipients for Freeze-Drying," *PDA J. Pharm. Sci. Technol.* 51:62-67, Parenteral Drug Association (1997).

Martini, A., et al., "Use of subambient differential scanning calorimetry to monitor the frozen state behaviour of amino acids in simulated freeze-drying conditions," *S.T.P. Pharma Sci.* 7:37-381, Editions de sante (1997).

Newman, M.J., et al., "Use of Nonionic Block Copolymers in Vaccines and Therapeutics," in: *Critical Reviews in Therapeutic Drug Carrier Systems*, Bruck, S.D., ed., Begell House, Inc. (1998).

Oliyai, C., et al., "Chemical Pathways of Peptide Degradation. VII. Solid State Chemical Instability of an Aspartyl Residue in a Model Hexapeptide," *Pharm. Res.* 11:901-908, Plenum Press (1994).

Orizio, G., et al., "Freeze-dried mannitol for injectable preparations using an automatic lyophilization cycle," *Boll. Chim. Farm.* 132:368-374, Società Editoriale Farmaceutica (1993).

Österberg, T., et al., "Development of a Freeze-Dried Albumin-Free Formulation of Recombinant Factor VIII SQ," *Pharm. Res.* 14:892-898, Plenum Press (1997).

Todd, C.W., et al., "Development of an adjuvant-active nonionic block copolymer for use in oil-free subunit vaccines formulations," *Vaccine* 15:564-570, Elsevier Science Ltd. (1997).

Todd, C.W., et al., "Systemic Development of a Block Copolymer Adjuvant for Trivalent Influenza Virus Vaccine," *Dev. Biol. Stand.* 92:341-351, Karger (1998).

Tse, C. and Capeau, J., "Quantification des acides nucléiques par PCR quantitative en temps réel," *Ann. Biol. Clin.* 61:279-293, John Libbet Eurotext (May-Jun. 2003).

Wade, A. and Weller, P.J., eds., "Benzalkonium Chloride," "Benzethonium Chloride," "Cetrimide," in: *Handbook of Pharmaceutical Excipients*, American Pharmaceutical Association, Washington, DC, pp. 27-31, 96-98 (1994).

Co-Pending U.S. Appl. No. 09/478,457, Wolff et al., filed Jan. 6, 2000 (Not Published).

Molina, M.C. et al., "Maintenance of nonviral vector particle size during the freezing step of the lyophilization process is insufficient for preservation of activity: insight from other structural indicators." *J. Pharma. Sci.* 90:1445-1455, Wiley-Liss, Inc (Oct. 2001).

Cherng, J.Y., "Stabilization of polymer-based gene delivery systems." *Int. J. Pharma.* 183:25-28, Elsevier B.V. (Jun. 1999).

Baumgartner, I., et al., "Constitutive Expression of phVEGF$_{165}$ After Intramuscular Gene Transfer Promotes Collateral Vessel Development in Patients With Critical Limb Ischemia," *Circulation* 97:1114-1123, Lippincott, Williams, & Wilkins (1998).

Chen, Z-Y., et al., "Linear DNAs Concatemerize in Vivo and Result in Sustained Transgene Expression in Mouse Liver," *Mol. Ther.* 3:403-410, Academic Press (Mar. 2001).

Cheng, S.H., and Scheule, R.K., "Airway delivery of cationic lipid: DNA complexes for cystic fibrosis," *Adv. Drug Deliv. Rev.* 30:173-184, Elsevier Science B.V. (1998).

Cherng, J.-Y., et al., "Effect of DNA topology on the transfection efficiency of poly((2-dimethylamino)ethyl methacrylate)-plasmid complexes," *J. Control. Release* 60:343-353, Elsevier Science B.V. (1999).

Dalesandro, J., et al., "Gene Therapy for Donor Hearts: Ex Vivo Liposome-Mediated Transfection," *J. Thorac. Cardiovasc. Surg.* 111:416-422, Mosby-Year Book, Inc. (1996).

Danko, I., et al., "Dystrophin expression improves myofiber survival in *mdx* muscle following intramuscular plasmid DNA injection," *Hum. Mol. Genet.* 2:2055-2061, Oxford University Press (1993).

Darquet, A.-M., et al., "A new DNA vehicle for nonviral gene delivery: supercoiled minicircle," *Gene Ther.* 4:1341-1349, Nature Publishing Group (1997).

Davis, H.L., et al., "Direct gene transfer in skeletal muscle: plasmid DNA-based immunization against the hepatitis B virus surface antigen," *Vaccine* 12:1503-1509, Butterworth-Heinemann Ltd. (1994).

Dow, S.W., et al., "Systemic and Local Interferon γ Gene Delivery to the Lungs for Treatment of Allergen-Induced Airway Hyperresponsiveness in Mice," *Hum. Gene Ther.* 10:1905-1914, Mary Ann Liebert, Inc. (1999).

Gramzinski, R., et al., "Immune Response to a Hepatitis B DNA Vaccine in *Aotus* Monkeys: A Comparison of Vaccine Formulation, Route, and Method of Administration," *Mol. Med.* 4:109-118, The Picower Institute Press (1998).

Harland, R., and Misher, L., "Stability of RNA in developing *Xenopus* embryos and identification of a destabilizing sequence in TFIIIA messenger RNA," *Development* 102:837-852, The Company of Biologists Limited (1988).

Horton, H.M., et al., "A gene therapy for cancer using intramuscular injection of plasmid DNA encoding interferon α," *Proc. Natl. Acad. Sci. USA* 96:1553-1558, National Academy of Sciences (1999).

Levy, M.Y., et al., "Characterization of plasmid DNA transfer into mouse skeletal muscle: evaluation of uptake mechanism, expression and secretion of gene products into blood," *Gene Ther.* 3:201-211, Nature Publishing Group (1996).

Mir, L.M., et al., "High-efficiency gene transfer into skeletal muscle mediated by electric pulses," *Proc. Natl. Acad. Sci. USA* 96:4262-4267, National Academy of Sciences (1999).

Moffatt, M., and Cookson, W., "Naked DNA: New shots for allergy?," *Nat. Med.* 2:515-516, Nature America Inc. (1996).

Novo, F.J., et al., "Gene transfer and expression of human α-galactosidase from mouse muscle in vitro and in vivo," *Gene Ther.* 4:488-492, Nature Publishing Group (1997).

Pelletier, J., and Sonenberg, N., "Internal initiation of translation of eukaryotic mRNA directed by a sequence derived from poliovirus RNA," *Nature* 334:320-325, Macmillan Magazines Ltd. (1988).

Piccirillo, C.A., and Prud'homme, G.J., "Prevention of Experimental Allergic Encephalomyelitis by Intramuscular Gene Transfer with Cytokine-Encoding Plasmid Vectors," *Hum. Gene Ther.* 10:1915-1922, Mary Ann Liebert, Inc. (1999).

Piccirillo, C.A., et al., "TGF-β1 Somatic Gene Therapy Prevents Autoimmune Disease in Nonebese Diabetic Mice," *J. Immunol. 161*:3950-3956, The American Association of Immunologists (1998).

Qin, L., et al., "Gene Transfer for Transplantation—Prolongation of Allograft Survival with Transforming Growth Factor-β1," *Ann. Surg. 220*:508-519, J.B. Lippincott Company (1994).

Qin, Y.-J., et al., "Gene Suture—A Novel Method for Intramuscular Gene Transfer and its Application in Hypertension Therapy," *Life Sci. 65*:2193-2203, Elsevier Science Inc. (1999).

Ragno, S., et al., "Protection of Rats from Adjuvant Arthritis by Immunization with Naked DNA Encoding for Mycobacterial Heat Shock Protein 65," *Arthritis Rheum. 40*:277-283, American College of Rheumatology (1997).

Restifo, N.P., et al., "Ehancing the Recognition of Tumour Associated Antigens," *Folia Biologica 40*:74-88, Institute of Molecular Genetics (1994).

Schrijver, R.S., et al., "Immunization of cattle with a BHV1 vector vaccine or a DNA vaccine both coding for the G protein of BRSV," *Vaccine 15*:1908-1916, Elsevier Science Ltd. (1997).

Tripathy, S.K., et al., "Long-term expression of erythropoietin in the systemic circulation of mice after intramuscular injection of a plasmid DNA vector," *Proc. Natl. Acad. Sci. USA 93*:10876-10880, National Academy of Sciences (1996).

Tsurumi, Y., et al., "Direct Intramuscular Gene Transfer of Naked DNA Encoding Vascular Endothelial Growth Factor Augments Collateral Development and Tissue Perfusion," *Circulation 94*:3281-3290, Lippincott, Williams, & Wilkins (1996).

Ulmer, J.B., et al., "Immunization Against Viral Proteins with Naked DNA," *Ann. N.Y. Acad. Sci. 772*:117-125, New York Academy of Sciences (1995).

Vahlsing, H.L., et al., "Immunization with plasmid DNA using a pneumatic gun," *J. Immunol. Methods 175*:11-22, Elsevier Science B.V. (1994).

Yagi, K., et al., "Basic Study on Gene Therapy of Human Malignant Glioma by Use of the Cationic Multilamellar Liposome-Entrapped Human Interferon β Gene," *Hum. Gene Ther. 10*:1975-1985, Mary Ann Liebert, Inc. (1999).

* cited by examiner

BAK C$_{12}$

Bn-DHRIE

DHxRIE-OAc

DHxRIE-OBz

Pr-DOctRIE-OAc

METHOD FOR FREEZE-DRYING NUCLEIC ACID/BLOCK COPOLYMER/CATIONIC SURFACTANT COMPLEXES

CROSS-REFERENCE TO RELATED APPLICATION

The present application claims the benefit of the filing date of U.S. Provisional Application No. 60/435,273 filed Dec. 23, 2002, which is incorporated herein by reference in its entirety.

BACKGROUND OF THE INVENTION

1. Field of the Invention

This invention relates generally to the freeze-drying of formulations comprising a polynucleotide, a block copolymer and a cationic surfactant. In the presence of a cryoprotectant or bulking agent, a formulation can be freeze-dried, whereby upon reconstitution of the dried formulation, the microparticles maintain their optimal size and aggregation or fusion is avoided.

2. Related Art

The use of non-ionic block copolymers as adjuvants in polynucleotide based medicaments has been documented in the art. Polynucleotide complexes which comprise a polynucleotide, a block copolymer and a cationic surfactant have demonstrated enhanced in vivo immune response. In some cases, it is desirable or necessary to supply a suspension of these complexes in a dry powder form that can be reconstituted to an aqueous system just prior to use. One method of drying an aqueous medium is by lyophilization in which the medium is frozen and then the water is extracted by sublimation under vacuum. If the aqueous medium contains a suspension of microparticles, these microparticles tend to cluster during the initial freezing step of the lyophilization process due to the propagation of the crystallization front. Often, the microparticles become permanently aggregated and do not redisperse when reconstituted, creating a population with a very polydisperse size distribution.

Methods for controlling aggregation during freeze-drying and reconstitution through the use of cryoprotectants and bulking agents or other excipients are known in the art and have been described for liposome formulations (See U.S. Pat. No. 5,817,334, hereby incorporated by reference in its entirety), microparticles (See U.S. Pat. No. 6,482,581, hereby incorporated by reference in its entirety) and nucleic acid-polycation compositions (See U.S. Pat. No. 6,251,599, hereby incorporated by reference in its entirety).

Despite these advances, there exists a need for methods by which to freeze-dry and reconstitute compositions comprising a polynucleotide and a block copolymer that also contain a cationic surfactant, such that the same particle size and population polydispersity prior to freeze-drying are maintained following reconstitution. The present invention fulfills this need.

BRIEF SUMMARY OF THE INVENTION

In one aspect, the invention provides a method of preparing a lyophilized composition comprising mixing a block copolymer with a population of polynucleotide molecules, a cationic surfactant, and an amorphous cryoprotectant or a bulking agent or any combination thereof, at a temperature below the cloud point of the block copolymer to form a mixture. This mixture is then frozen and finally dried under vacuum. Upon reconstitution of this mixture, the particle size and population polydispersity are maintained.

In a further embodiment, the composition comprising a polynucleotide, a block copolymer and a cationic surfactant are mixed at a temperature below the cloud point of the block copolymer, at a temperature of about −2° C. to about 8° C. In yet another aspect of the invention, prior to lyophilization, the mixture is cold filtered, thereby rendering it sterile. Suitably, this cold filtration step is performed at a temperature of about −2° C. to about 8° C. using a filter with a pore size of about 0.01 microns to about 2 microns.

Block copolymers such as polyoxyethylene (POE)/polyoxypropylene (POP) are desired. An example of a useful block copolymer is Poloxamer CRL-1005. Suitable cationic surfactants for use in the present invention include benzalkonium chloride and (±)-N-(3-Acetoxypropyl)-N,N-dimethyl-2,3-bis(octyloxy)-1-propanaminium chloride (Pr-DoctRIe-OAc).

Suitable amorphous cryoprotectants and crystalline bulking agents include the following sugars: sucrose, lactose, trehalose, maltose or glucose, wherein the solution comprises about 1% to about 20% (w/v) sugar. A suitable embodiment of the invention contains about 10% sucrose. The composition may also optionally comprise a pH stabilizing buffer.

The present invention also encompasses the polynucleotide/block copolymer/cationic surfactant microparticles produced by the lyophilization processes described herein.

BRIEF DESCRIPTION OF THE DRAWINGS/FIGURES

Figure 1B:
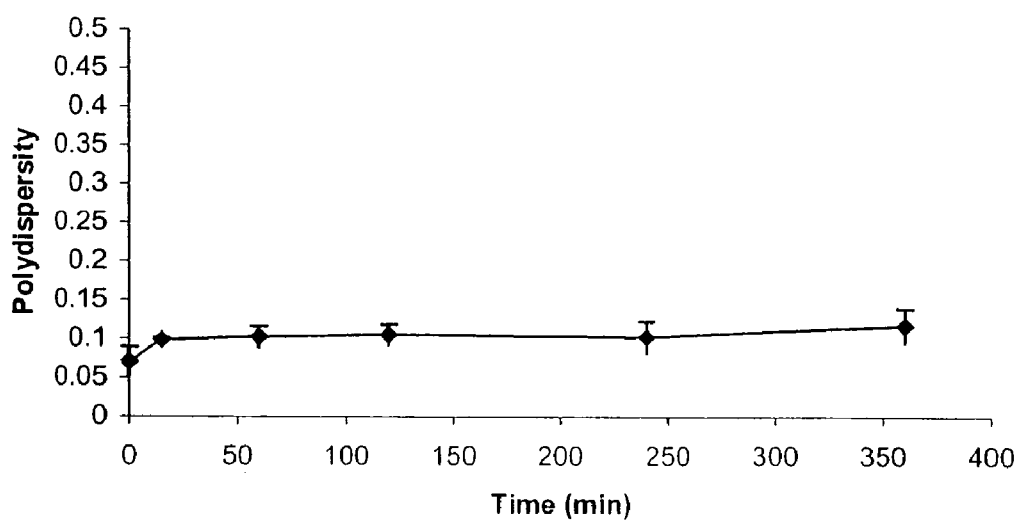

FIG. 1A and FIG. 1B are graphs plotting the Z average mean particle size and polydispersity of reconstituted lyophilized microparticles produced by the method described in Example 1.

Figure 2:
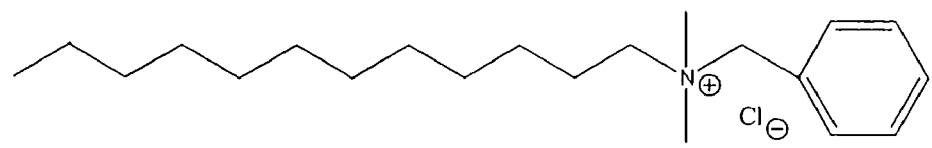
Figure 2:
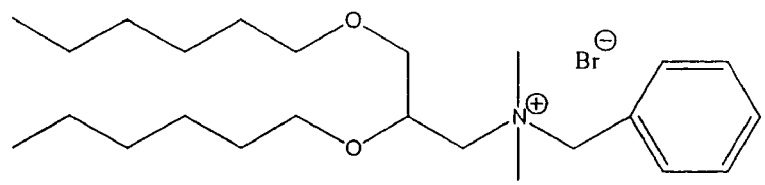
Figure 2:
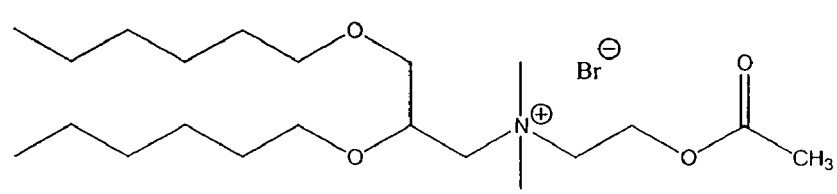
Figure 2:
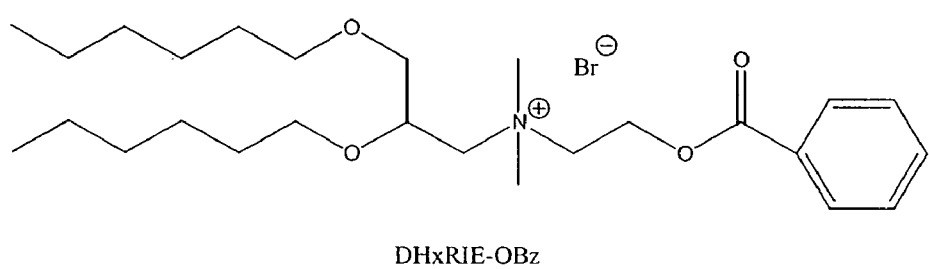
Figure 2:
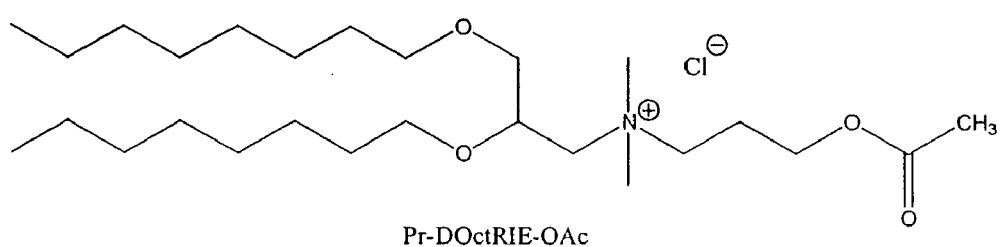

FIG. 2 contains the structures of the following cationic lipids: Benzalkonium chloride (BAK C12), (±)-N-(Benzyl)-N,N-dimethyl-2,3-bis(hexyloxy)-1-propanaminium bromide (Bn-DHxRIE), (±)-N-(2-Acetoxyethyl)-N,N-dimethyl-2,3-bis(hexyloxy)-1-propanaminium bromide (DHxRIE-OAc), (±)-N-(2-Benzoyloxyethyl)-N,N-dimethyl-2,3-bis(hexyloxy)-1-propanaminium bromide (DHxRIE-OBz) and (±)-N-(3-Acetoxypropyl)-N,N-dimethyl-2,3-bis(octyloxy)-1-propanaminium chloride (Pr-DOctRIE-OAc).

DETAILED DESCRIPTION OF THE INVENTION

Definitions

As used herein, "PBS" refers to—phosphate buffered saline—.

As used herein, "BAK" refers to—benzalkonium chloride—.

As used herein, "BEC" refers to—benzethonium chloride—.

As used herein, "CPC" refers to—cetylpyridinium chloride—.

As used herein, "CTAC" refers to—cetyl trimethyl-ammonium chloride—.

As used herein, "PS-80" refers to—polysorbate 80—.

As used herein, the term "cloud point" refers to the point in a temperature shift, or other titration, at which a clear solution becomes cloudy, i.e., when a component dissolved in a solution begins to precipitate out of solution.

As used herein, the words "particle" and "microparticle" are interchangeable.

As used herein, the words "mixture" and "solution" are interchangeable.

As used herein, the term "adjuvant" is any substance or combination of substances which nonspecifically enhances the immune response to an antigen; and also relates to any substance which enhances the immune response directly related to delivery of a polynucleotide within a vertebrate or mammalian host, such as a human or non-human mammalian host, such that administration of the adjuvant in combination with the polynucleotide results in an increased in vivo immune response to expression of the intended antigen or antigens encoded by the polynucleotide. Included in this definition are substances which may act as facilitators of gene delivery, thereby increasing the amount of plasmid DNA delivered to cells that can express the intended antigen. Substances which may enhance delivery of plasmid DNA would include those which do not substantially interact with the plasmid DNA in the formulation and substances which do interact with the plasmid DNA, forming tightly bound or weakly bound complexes between the adjuvant and the plasmid DNA, either in vitro or in vivo.

As used herein, the term "polynucleotide" is a nucleic acid molecule which contains essential regulatory elements such that upon introduction into a living, vertebrate cell, the nucleic acid molecule is able to direct the cellular machinery to produce translation products encoded by the genes comprising the nucleic acid molecule.

As used herein, the term "polynucleotide medicament" is used to indicate polynucleotide-based compositions, including compositions which comprise the poloxamers and cationic surfactants disclosed herein, useful as a vehicle to deliver a transgene of interest to a vertebrate host, such as a human or non-human mammalian host, or to provide or promote detectable and/or therapeutic levels of expression of the transgene, and/or to generate or promote an immune response to the expression product of the transgene.

As used herein, the term "vector" refers to a vehicle by which DNA fragments, most likely comprising a transgene or portion thereof which expresses an antigen or antigenic epitope, can be introduced into a host organism or host tissue. There are various types of vectors which include but are not limited to recombinant vectors, including DNA plasmid vectors, recombinant viral vectors such as adenovirus vectors, retrovirus vectors and adeno-associated virus vectors, as well as bacteriophage vectors and cosmid vectors.

The term "gene" or "transgene" refers to a segment of a nucleic acid molecule which encodes a discrete protein or a portion thereof, such as a portion of the full-length protein which will induce an appropriate immune response within the host.

As used herein, the term "amorphous cryoprotectant" refers to a compound which, when included in the formulations of the present invention during freezing or lyophilization under given conditions, does not form crystals. It is specifically intended that compounds that are known to form crystals under certain lyophilization conditions but not under others are included within the term "amorphous cryoprotectant," so long as they remain amorphous under the specific freezing or lyophilization conditions to which they are subjected. The term "cryoprotectant" may be used interchangeably with the term "amorphous cryoprotectant" herein.

As used herein, "crystalline bulking agent" refers to a compound which, when included in the formulations of the present invention during freezing or lyophilization under given conditions, forms crystals. It is specifically intended that compounds that are known to form crystals under certain lyophilization conditions but not under others are included within the term "crystalline bulking agent," so long as they crystallize under the specific freezing or lyophilization conditions to which they are subjected. The term "bulking agent" may be used interchangeably with the term "crystalline bulking agent" herein.

As used herein, "lyophilization" is a means of drying, achieved by freezing a wet substance at a temperature from about −172° C. to about −2° C. followed by rapid dehydration by sublimation under a vacuum level down to the lower level of a diffusion pump. A useful pressure range is from about 0.1 mTorr to about 0.5 Torr. The term "freeze-drying" may be used interchangeably with the term "lyophilization" herein.

Amorphous cryoprotectants, crystalline bulking agents, and methods of determining the same are known and available in the art. The following articles, incorporated herein by reference, provide a basic teaching in this regard: Osterberg et al., *Pharm Res* 14(7):892-898 (1997); Oliyai et al., *Pharm Res* 11(6):901-908 (1994); Corveleyn et al., *Pharm Res* 13(1):146-150 (1996); Kim et al., *J Pharm Sciences* 87(8): 931-935 (1998); Martini et al., *PDA J Pharm Sci Tech* 51(2): 62-67 (1997); Martini et al., *STP Pharma Sci.* 7(5):377-381 (1997); and Orizio et al., *Boll. Chim. Farm.* 132(9):368-374 (1993).

The present invention relates to novel methods for lyophilizing a formulation suitable for use in polynucleotide based medicaments. The methods result in formulations comprising polynucleotide molecules, block copolymer, and a cationic surfactant that upon reconstitution maintain the same particle size and polydispersity prior to freeze-drying.

The method of the present invention comprises mixing: (i) a cationic surfactant; (ii) a block copolymer; and (iii) a polynucleotide; at a temperature below the cloud point of said block copolymer to form a mixture. The order in which components of the mixture are added may vary. A suitable order in which ingredients of the mixture may be added include, but is not limited to, (i) polynucleotide; (ii) block copolymer; and (iii) cationic surfactant. Alternatively, the order of addition can also include: (i) cationic surfactant; (ii) block copolymer; and (iii) polynucleotide. Stirring of the mixture can occur once all components have been added, concurrently while components are being added, or in between the addition of components.

The block copolymers useful in the polynucleotide based medicaments described herein are block copolymers which form microparticles at room temperature (above the block copolymer cloud point) and may associate with a population of nucleic acid molecules, such as a population of plasmid DNA molecules, with and without the addition of cationic surfactants. The nucleic acid molecules of the present invention may include a deoxyribonucleic acid molecule (DNA), such as genomic DNA and complementary DNA (cDNA) as well as a ribonucleic acid molecule (RNA). In regard to the block copolymer, a suitable group of copolymers used in the methods of the present invention include non-ionic block copolymers which comprise blocks of polyoxyethylene (POE) and polyoxypropylene (POP).

While the invention contemplates the use of any such block copolymer which promotes generation of a particle size and surface charge as described herein, suitable non-ionic block copolymers include polyoxyethylene (POE)/polyoxypropylene (POP) block copolymers, especially higher molecular weight POE-POP-POE block copolymers. These compounds are described in U.S. Reissue Pat. No. 36,665, U.S. Pat. Nos. 5,567,859, 5,691,387, 5,696,298 and 5,990,241, and Published International Patent Application WO 96/04392, all of which are hereby incorporated by reference.

Briefly, these non-ionic block copolymers have the following general formula: $HO(C_2H_4O)_x(C_3H_6O)_y(C_2H_4O)_xH$ wherein (y) represents a number such that the molecular weight of the hydrophobic POP portion ($C_3H_6O$) is up to approximately 20,000 daltons and wherein (x) represents a number such that the percentage of hydrophilic POE portion ($C_2H_4O$) is between approximately 1% and 50% by weight.

A suitable POE-POP-POE block copolymer that can be used in the invention has the following formula $HO(C_2H_4O)_x(C_3H_6O)_y(C_2H_4O)_xH$ wherein (y) represents a number such that the molecular weight of the hydrophobe ($C_3H_6O$) is between approximately 9,000 Daltons and 15,000 Daltons and (x) represents a number such that the percentage of hydrophile ($C_2H_4O$) is between approximately 3% and 35%.

Another suitable POE-POP-POE block copolymer that can be used in the invention has the following formula: $HO(C_2H_4O)_x(C_3H_6O)_y(C_2H_4O)_xH$ wherein (y) represents a number such that the molecular weight of the hydrophobe ($C_3H_6O$) is between approximately 9,000 Daltons and 15,000 Daltons and (x) represents a number such that the percentage of hydrophile ($C_2H_4O$) is between approximately 3% and 10%.

A typical POE/POP block copolymer utilized herein will comprise the structure of POE-POP-POE, as reviewed in Newman et al. *Critical Reviews in Therapeutic Drug Carrier Systems* 15 (2): 89-142 (1998). A suitable block copolymer for use in the methods of the present invention is a POE-POP-POE block copolymer with a central POP block having a molecular weight in a range from under 1000 daltons up to approximately 20,000 daltons and flanking POE blocks which comprise up to about 50% of the total molecular weight of the copolymer. Block copolymers such as these, which are much larger than earlier disclosed Pluronic-based POE/POP block copolymers, are described in detail in U.S. Reissue Pat. No. 36,655. A representative POE-POP-POE block copolymer utilized to exemplify DNA formulations of the present invention is disclosed in Published International Patent Application No. WO 96/04392, is also described at length in Newman et al. (Id.), and is referred to as CRL-1005 (CytRx Corp).

CRL-1005 is another suitable surface-active copolymer that can be used in the invention and has the following formula: $HO(C_2H_4O)_x(C_3H_6O)_y(C_2H_4O)_xH$ wherein (y) represents a number such that the molecular weight of the hydrophobe ($C_3H_6O$) is approximately 12,000 Daltons and (x) represents a number such that the percentage of hydrophile ($C_2H_4O$) is approximately 5%. In the case of CRL-1005, (x) is about 7, ±1 and (y) is approximately 12,000 Daltons, with about 207 units, ±7.

Although there is evidence to suggest that the association of plasmid DNA to the CRL-1005 particles leads to an improved immune response, the mechanism by which the immune response is enhanced is at present unclear. While not being bound by theory in any way, it is possible that DNA associated to CRL-1005 particles may be more readily taken up and expressed by cells. It is also possible that the negative surface charge of the CRL-1005 particles, produced by the association of plasmid DNA to CRL-1005/BAK particles, may be important for enhancing the adjuvant properties of CRL-1005. The current invention does not distinguish between these two possible mechanisms of enhancing the immune response.

The measurement of surface charge (zeta potential) and the amount of DNA associated with CRL-1005 particles are consistent with a model for the interaction of plasmid DNA/the block copolymer (CRL-1005) and the cationic surfactant (for example, BAK). The model suggests that BAK associating with particles of CRL-1005, through hydrophobic interactions, results in a reduction of the CRL-1005 particle size and in the formation of positively charged CRL-1005 particles. Association of the polynucleotide (plasmid DNA) is believed to occur through electrostatic interactions between the positively charged headgroup of the cationic surfactant (BAK) and the DNA phosphate groups, while the hydrophobic tail of the cationic surfactant is embedded within the block copolymer (CRL-1005) particle.

Published International Patent Application WO 02/00844 discloses that the generation of physically distinct particles comprising the block co-polymer CRL-1005, a cationic surfactant and DNA, further promotes the association of plasmid DNA to the block copolymer as compared to the block co-polymer and DNA alone. The particles containing all three components also resulted in a marked enhancement of a cellular immune response.

An alternative surface-active copolymer that can be used in the invention has the following formula: $HO(C_2H_4O)_x(C_3H_6O)_y(C_2H_4O)_xH$ wherein (y) represents a number such that the molecular weight of the hydrophobe ($C_3H_6O$) is approximately 9,000 Daltons and (x) represents a number such that the percentage of hydrophile ($C_2H_4O$) is approximately 3-5%.

Another suitable surface-active copolymer that can be used in the invention has the following formula: $HO(C_2H_4O)_x(C_3H_6O)_y(C_2H_4O)_xH$ wherein (y) represents a number such that the molecular weight of the hydrophobe ($C_3H_6O$) is approximately 9,000 Daltons and (x) represents a number such that the percentage of hydrophile ($C_2H_4O$) is approximately 3%.

In yet another alternative embodiment the present invention relates to a method for producing a lyophilized formulation suitable for use in polynucleotide based medicaments comprising a block copolymer which is Poloxamer CRL-1005.

Another suitable group of block copolymers for use in the present invention include "reverse" block copolymers wherein the hydrophobic portions of the molecule ($C_3H_6O$) and the hydrophilic portions ($C_2H_4O$) have been reversed such that the polymer has the formula: $HO(C_3H_6O)_y(C_2H_4O)_x(C_3H_6O)_yH$ wherein (y) represents a number such that the molecular weight of the hydrophobic POP portion ($C_3H_6O$) is up to approximately 20,000 daltons and wherein (x) represents a number such that the percentage of hydrophilic POE portion ($C_2H_4O$) is between approximately 1% and 50% by weight. These "reverse" block copolymers have the structure POP-POE-POP and are described in U.S. Pat. Nos. 5,656,611 and 6,359,054.

A suitable POP-POE-POP block copolymer that can be used in the invention has the following formula: $HO(C_3H_6O)_y(C_2H_4O)_x(C_3H_6O)_yH$ wherein (y) represents a number such that the molecular weight of the hydrophobe ($C_3H_6O$) is between approximately 9,000 Daltons and 15,000 Daltons and (x) represents a number such that the percentage of hydrophile ($C_2H_4O$) is between approximately 3% and 35%.

Another suitable POP-POE-POP block copolymer that can be used in the invention has the following formula: $HO(C_3H_6O)_y(C_2H_4O)_x(C_3H_6O)_yH$ wherein (y) represents a number such that the molecular weight of the hydrophobe ($C_3H_6O$) is between approximately 9,000 Daltons and 15,000 Daltons and (x) represents a number such that the percentage of hydrophile ($C_2H_4O$) is between approximately 3% and 10%.

Another suitable surface-active copolymer that can be used in the invention and has the following formula: $HO(C_3H_6O)_y(C_2H_4O)_x(C_3H_6O)_yH$ wherein (y) represents a number such that the molecular weight of the hydrophobe ($C_3H_6O$) is approximately 12,000 Daltons and (x) represents a number such that the percentage of hydrophile ($C_2H_4O$) is approximately 5%.

An alternative surface-active copolymer that can be used in the invention has the following formula: $HO(C_3H_6O)_y$-$(C_2H_4O)_x(C_3H_6O)_yH$ wherein (y) represents a number such that the molecular weight of the hydrophobe ($C_3H_6O$) is approximately 9,000 Daltons and (x) represents a number such that the percentage of hydrophile ($C_2H_4O$) is approximately 3-5%.

Another suitable surface-active copolymer that can be used in the invention has the following formula: $HO(C_3H_6O)_y$-$(C_2H_4O)_x(C_3H_6O)_yH$ wherein (y) represents a number such that the molecular weight of the hydrophobe ($C_3H_6O$) is approximately 9000 Daltons and (x) represents a number such that the percentage of hydrophile ($C_2H_4O$) is approximately 3%.

The block copolymers for use in the invention are amphipathic compounds with inverse solubility characteristics in aqueous media. Below their cloud points (1-20° C.), these copolymers are water-soluble and form clear solutions that can be filter sterilized. The solution process involves the formation of hydrogen bonds between oxygen atoms and hydroxyl groups in the copolymer and water molecules. When a solution of copolymer is warmed and passes through its cloud point, the increased thermal motion is sufficient to break the hydrogen bonds and as the copolymer comes out of solution, they self-assemble into microparticles (See Todd, C. W., et al. *Vaccine* 15: 564-570 (1997) and Todd, C. W., et al. *Dev. Biol. Stand.* 92: 343-353 (1997)). The process is reversible.

Any type of polynucleotide can be incorporated into the method of the current invention. For example plasmid DNA, genomic DNA, cDNA, DNA fragments and RNA. Certain formulations of the present invention include a cocktail of plasmids. Various plasmids desired in a cocktail are combined together in PBS or other diluent prior to addition to the other ingredients. There is no upper limit to the number of different types of plasmids which can be used in the methods of the present invention. Furthermore, plasmids may be present in a cocktail at equal proportions, or the ratios may be adjusted based on, for example, relative expression levels of the antigens or the relative immunogenicity of the encoded antigens. Thus, various plasmids in the cocktail may be present in equal proportion, or 2, 3, 4, 5, 6, 7, 8, 9, 10 or more times as much of one plasmid may be included relative to other plasmids in the cocktail.

The polynucleotide formulations produced by the methods of the present invention also comprise a cationic surfactant. It will be known to one of skill in the art that numerous cationic surfactants may be a candidate for use in these formulations. Therefore, the invention contemplates use of any cationic surfactant which, along with a block copolymer, and a polynucleotide promotes generation of a particle size and surface charge as described herein. Cationic surfactants which may be used include, but are not limited to, benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC) and cetyl trimethylammonium chloride (CTAC), primary amines, secondary amines, tertiary amines, including but not limited to N,N',N'-polyoxyethylene (10)-N-tallow-1,3-diaminopropane, other quaternary amine salts, including but not limited to dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2(2-methyl-4-(1,1,3,3tetramethylbutyl)-phenoxy]-ethoxy)ethyl]-benzenemethanaminium chloride (DEBDA), dialkyldimetylammonium salts, -[1-(2,3-dioleyloxy)-propyl]-N,N,N, trimethylammonium chloride, 1,2-diacyl-3-(trimethylammonio) propane (acyl group=dimyristoyl, dipalmitoyl, distearoyl dioleoyl), 1,2-diacyl-3 (dimethylammonio) propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl3-succinyl-sn-glycerol choline ester, cholesteryl (4'-trimethylammonio)butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkylglycetylphosphorylcholine, lysolecithin, L-adioleoyl phosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group ($C_{12}GluPhCnN^+$), ditetradecyl glutamate ester with pendant amino group ($C_{14}GluCnN^+$), cationic derivatives of cholesterol, including but not limited to cholesteryl-3β-oxysuccinamidoethylenetrimethylammonium salt, cholesteryl-3β-oxysuccinamidoethylenedimethylamine, cholesteryl-3β-carboxyamidoethylenetrimethylammonium salt, cholesteryl-3β-carboxyamidoethylenedimethylamine, and 3β-[N-(N',N'-dimethylaminoetanecarbomoyl)cholesterol](DC-Chol).

Other examples of cationic surfactants for use in the invention are selected from the group of cationic lipids including N-(3-aminopropyl)-N,N-(bis-(2-tetradecyloxyethyl))-N-methyl-ammonium bromide (PA-DEMO), N-(3-aminopropyl)-N,N-(bis-(2-dodecyloxyethyl))-N-methyl-ammonium bromide (PA-DELO), N,N,N-tris-(2-dodecyloxy)ethyl-N(3-amino)propyl-ammonium bromide (PA-TELO), and $N^1$-(3-aminopropyl) ((2-dodecyloxy)ethyl)-$N^2$-(2-dodecyloxy) ethyl-1-piperazinaminium bromide (GA-LOE-BP), DL-1,2-dioleoyl-3-dimethylaminopropyl-β-hydroxyethylammonium (DORI diester), and 1-O-oleyl-2-oleoyl-3-dimethylaminopropyl-β-hydroxyethylammonium (DORI ester/ether).

Additional suitable, but non-limiting cationic lipids for use in certain embodiments of the present invention include DMRIE ((±)-N-(2-hydroxyethyl)-N,N-dimethyl-2,3-bis(tetradecyloxy)-1-propanaminium bromide), GAP-DMORIE ((±)-N-(3-aminopropyl)-N,N-dimethyl-2,3-bis(syn-9-tetradeceneyloxy)-1-propanaminium bromide), and GAP-DLRIE ((±)-N-(3-aminopropyl)-N,N-dimethyl-2,3-(bis-dodecyloxy)-1-propanaminium bromide).

Other cationic lipids for use in the present invention include the compounds described in U.S. Pat. Nos. 5,264,618, 5,459,127 and 5,994,317. Non-limiting examples of these cationic lipids include (±)-N,N-dimethyl-N-[2-(sperminecarboxamido)ethyl]-2,3-bis(dioleyloxy)-1-propaniminium pentahydrochloride (DOSPA), (±)-N-(2-aminoethyl)-N,N-dimethyl-2,3-bis(tetradecyloxy)-1-propaniminium bromide (β-aminoethyl DMRIE or βAE-DMRIE) and (±)-N-(3-aminopropyl)-N,N-dimethyl-2,3-bis(dodecyloxy)-1-propaniminium bromide (GAP-DLRIE).

Other examples of DMRIE-derived cationic lipids that are useful in the present invention include (±)-N-(3-aminopropyl)-N,N-dimethyl-2,3-(bis-decyloxy)-1-propanaminium bromide (GAP-DDRIE), (±)-N-(3-aminopropyl)-N,N-dimethyl-2,3-(bis-tetradecyloxy)-1-propanaminium bromide (GAP-DMRIE), (±)-N-((N"-methyl)-N'-ureyl)propyl-N,N-dimethyl-2,3-bis(tetradecyloxy)-1-propanaminium bromide (GMU-DMRIE), (±)-N-(2-hydroxyethyl)-N,N-dimethyl-2,3-bis(dodecyloxy)-1-propanaminium bromide (DLRIE), and (±)-N-(2-hydroxyethyl)-N,N-dimethyl-2,3-bis-([Z]-9-octadecenyloxy)propyl-1-propaniminium bromide (HP-DO-RIE).

In a suitable aspect of the present invention, the cationic surfactant is selected from the group consisting of benzalkonium chloride, benzethonium chloride, cetramide, cetylpyridinium chloride and cetyl trimethylammonium-chloride. Benzalkonium chloride is available commercially and is known to exist as a mixture of alkylbenzyldimethylammonium chlorides of the general formula: $[C_6H_5CH_2N(CH_3)2R]$ Cl, where R represents a mixture of alkyls, including all or some of the group beginning with n-$C_8H_{17}$ through n-$C_{16}H_{33}$. The average MW of BAK is 360 (see Handbook of Pharmaceutical Excipients, Ed. Wade and Weller, 1994, 2nd Ed. at page 27-29). Benzethonium chloride is N, N-dimethyl-N-[2-[2-[4-(1,1,3,3tetramethylbutyl)phenoxy]ethoxy]ethyl]benzene-methanaminium chloride ($C_{27}H_{42}ClNO_2$), which has a molecular weight of 448.10 (*Handbook of Pharmaceutical Excipients* at page 30-31). Cetramide consists mainly of trimethyltetradecylammonium bromide ($C_{17}H_{38}BrN$), which may contain smaller amounts of dodecyltrimethyl-ammonium bromide ($C_{15}H_{34}BrN$) and hexadecyltrimethylammonium bromide ($C_{19}H_{42}BrN$), and has a molecular weight of 336.40 (*Handbook of Pharmaceutical Excipients* at page 96-98).

In another suitable aspect of the present invention, the cationic surfactant for use in the methods of the current invention is selected from the group consisting of (±)-N-(Benzyl)-N,N-dimethyl-2,3-bis(hexyloxy)-1-propanaminium bromide (Bn-DHxRIE), (±)-N-(2-Acetoxyethyl)-N,N-dimethyl-2,3-bis(hexyloxy)-1-propanaminium bromide (DHxRIE-OAc), (±)-N-(2-Benzoyloxyethyl)-N,N-dimethyl-2,3-bis(hexyloxy)-1-propanaminium bromide (DHxRIE-OBz) and (±)-N-(3-Acetoxypropyl)-N,N-dimethyl-2,3-bis(octyloxy)-1-propanaminium chloride (Pr-DOctRIE-OAc). These lipids are disclosed in U.S. Provisional Application No. 60/435,303. In another suitable aspect of the present invention, the cationic surfactant is Pr-DOctRIE-OAc.

Auxiliary agents for use in compositions of the present invention include, but are not limited to, non-ionic detergents and surfactants IGEPAL CA 630® CA 630, NONIDET NP-40, Nonidet® P40, Tween-20®, Tween-80®, Triton X-100™, and Triton X-114™; the anionic detergent sodium dodecyl sulfate (SDS); the sugar stachyose; the condensing agent DMSO; and the chelator/DNAse inhibitor EDTA. In certain specific embodiments, the auxiliary agent is DMSO, Nonidet P40®. See, e.g., U.S. Patent Application Publication 20020019358, published Feb. 14, 2002, which is incorporated herein by reference in its entirety.

The polynucleotide formulations produced by the methods of the present invention may also optionally include a non-ionic surfactant, such as polysorbate-80, which may be a useful excipient to control particle aggregation in the presence of the polynucleotide. Additional non-ionic surfactants are known in the art and may be used to practice this portion of the invention. These additional non-ionic surfactants include, but are not limited to, other polysorbates, -Alkylphenyl polyoxyethylene ether, n-alkyl polyoxyethylene ethers (e.g., Tritons™), sorbitan esters (e.g., Spans™), polyglycol ether surfactants (Tergitol™), polyoxyethylenesorbitan (e.g., Tweens™), poly-oxyethylated glycol monoethers (e.g., Brij™, polyoxylethylene 9 lauryl ether, polyoxyethylene 10 ether, polyoxylethylene 10 tridecyl ether), lubrol, perfluoroalkyl polyoxylated amides, N,N-bis [3D-gluconamidopropyl] cholamide, decanoyl-N-methylglucamide, -decyl β-D-glucopyranozide, n-decyl β-D-glucopyranozide, n-decyl β-D-maltopyanozide, ndodecyl β-D-glucopyranozide, n-undecyl β-D-glucopyranozide, n-heptyl β-D-glucopyranozide, n-heptyl β-D-thioglucopyranozide, n-hexyl β-D-glucopyranozide, n-nonanoyl β-glucopyranozide 1-monooleyl-rac-glycerol, nonanoyl-N-methylglucamide, -dodecyl β-D-maltoside, N,N bis [3-gluconamidepropyl] deoxycholamide, diethylene glycol monopentyl ether, digitonin, hepanoyl-N-methylglucamide, octanoyl-N-methylglucamide, n-octyl β-D-glucopyranozide, n-octyl β-D-glucopyranozide, n-octyl β-D-thiogalactopyranozide, n-octyl β-D-thioglucopyranozide.

The present invention relates to methods for lyophilizing a formulation suitable for use in polynucleotide based medicaments such that upon reconstitution, the particle size and population polydispersity of the microparticles remain unchanged. The methods result in the generation of microparticles (at temperatures above the cloud point of CRL-1005, or another representative block copolymer) which comprise a block copolymer and cationic surfactant in contact with polynucleotide molecules. The components which will eventually comprise the microparticles are mixed with an amorphous cryoprotectant or a crystalline bulking agent by stirring at temperature below the cloud point of the block copolymer. Additionally, the mixture may also comprise a pH stabilizing buffer. Each component of this mixture must be thoroughly co-dissolved at a temperature below the cloud point of the polymer. This solution can also be sterilized via cold filtration and aliquoted into sterile vials prior to lyophilization. Prior to administration to a patient by injection, or any other means, the freeze-dried formulation can be reconstituted and the vial can be brought to room temperature or to a temperature above the cloud point of the block copolymer, wherein microparticle formation will occur during the warming process. It is the discovery of the current inventors that microparticle reconstitution results in particles with a particle size and a population polydispersity that remains unchanged during the freeze-drying process. This is further illustrated in Examples 1 and 2. Table 1 indicates the mean average diameter of microparticles composed of polynucleotide, poloxamer CRL-1005 and BAK co-dissolved in solutions of both PBS and 10% sucrose/10 mM sodium phosphate. The microparticles prepared in PBS have a much larger polydispersity following reconstitution than prior to freeze-drying indicating a broad size range of particles. In contrast, the microparticles co-dissolved in 10% sucrose/10 mM sodium phosphate demonstrate virtually the same polydispersity before lyophilization and after reconstitution, indicating a narrow size distribution. FIGS. 1a and 1b demonstrate that particle size and polydispersity remain unchanged after 6 hours at room temperature following reconstitution.

The lyophilized composition of the present invention may be reconstituted in any aqueous solution which produces a stable, mono-dispersed solution suitable for administration. Such aqueous solutions include, but are not limited to: sterile water, PBS or saline.

Upon review of this specification, the artisan will be able to mix and match various block copolymers, cationic surfactants, excipients, as well as utilize various concentrations of these components. The artisan will be able to measure in vitro structural characteristics of the formulation, as shown herein, which may be instructive in preparing such components for in vivo administration.

In suitable embodiments of the present invention a polynucleotide is mixed with the poloxamer CRL-1005, BAK (Benzalkonium chloride 50% solution, available from Ruger Chemical Co. Inc.) and an amorphous cryoprotectant or crystalline bulking agent. Additionally, the mixture may also comprise a pH stabilizing buffer. Suitable final concentrations of each component of the formulae are described in the examples, but for any of these methods, the concentrations of each component may be varied by basic stoichiometric calculations known by those of ordinary skill in the art to make a final solution having the desired concentrations.

In the method of the current invention, the concentration of the block copolymer is adjusted depending on, for example, transfection efficiency, expression efficiency, or immunogenicity. In suitable embodiments, the final concentration of the block copolymer is between about 1 mg/mL to about 75 mg/mL. Alternatively the final concentration of the block copolymer is between about 3 mg/mL to about 50 mg/mL, about 5 mg/mL to about 40 mg/mL, about 6 mg/mL to about 30 mg/mL. For example, about 6 mg/mL, about 6.5 mg/mL about 7 mg/mL, about 7.5 mg/mL, about 8 mg/mL, about 9 mg/mL, about 10 mg/mL, about 15 mg/mL, about 20 mg/mL, about 25 mg/mL, or about 30 mg/mL of the block copolymer.

In another suitable embodiment of the method of the current invention, the concentration of the poloxamer CRL-1005 is adjusted depending on, for example, transfection efficiency, expression efficiency, or immunogenicity. In suitable embodiments, the final concentration of the poloxamer CRL-1005 is between about 1 mg/mL to about 75 mg/mL. Alternatively the final concentration of the poloxamer CRL-1005 is between about 3 mg/mL to about 50 mg/mL, about 5 mg/mL to about 40 mg/mL, about 6 mg/mL to about 30 mg/mL. For example, about 6 mg/mL, about 6.5 mg/mL about 7 mg/mL, about 7.5 mg/mL, about 8 mg/mL, about 9 mg/mL, about 10 mg/mL, about 15 mg/mL, about 20 mg/mL, about 25 mg/mL, or about 30 mg/mL of CRL-1005. Similarly the concentration of DNA in the methods of the current invention is adjusted depending on many factors, including the amount of a formulation to be delivered, the age and weight of the subject, the delivery method and route and the immunogenicity of the antigen being delivered. In an alternative embodiment, the final concentration of DNA is from about 1 ng/mL to about 30 mg/mL of plasmid (or other polynucleotide). Alternatively, a formulation of the present invention may have a final concentration of DNA from about 0.1 mg/mL to about 20 mg/mL, or about 1 mg/mL to about 10 mg/mL. For example, the final DNA concentration may be about 1 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 7 mg/mL, about 8 mg/mL, about 9 mg/mL, about 10 mg/mL, or about 20 mg/mL.

Additionally, the concentration of the cationic surfactant may be adjusted depending on, for example, a desired particle size and improved stability. Indeed, in certain embodiments, the methods of the present invention include CRL-1005 and DNA, but are free of cationic surfactant. In general, cationic surfactant-containing formulations of the present invention are adjusted to have a final concentration of cationic surfactant from about 0.01 mM to about 5 mM. Suitably, a formulation of the present invention may have a final cationic surfactant concentration of about 0.06 mM to about 1.2 mM, or about 0.1 mM to about 1 mM, or about 0.2 mM to about 0.7 mM. For example, a formulation of the present invention may have a final cationic surfactant concentration of about 0.2 mM, about 0.3 mM, about 0.4 mM, about 0.5 mM, about 0.6 mM, or about 0.7 mM.

Additionally, the concentration of BAK may be adjusted depending on, for example, a desired particle size and improved stability. Indeed, in certain embodiments, the methods of the present invention include CRL-1005 and DNA, but are free of BAK. In general BAK-containing formulations of the present invention are adjusted to have a final concentration of BAK from about 0.01 mM to about 5 mM. Alternatively, a formulation of the present invention may have a final BAK concentration of about 0.06 mM to about 1.2 mM, or about 0.1 mM to about 1 mM, or about 0.2 mM to about 0.7 mM. For example, a formulation of the present invention may have a final BAK concentration of about 0.2 mM, about 0.3 mM, about 0.4 mM, about 0.5 mM, about 0.6 mM, or about 0.7 mM.

The total volume of the formulations produced by the methods of the current invention may be scaled up or down, by choosing apparatus of proportional size. Finally, in carrying out any of the methods described below, the three components of the formulation, BAK, CRL-1005, and plasmid DNA, may be added in any order.

The polynucleotide based medicaments produced by the methods of the present invention may be formulated in any pharmaceutically effective formulation for host administration. It will be useful to utilize pharmaceutically acceptable formulations which also provide long-term stability of the polynucleotide based medicaments of the present invention. During storage as a pharmaceutical entity, DNA plasmids undergo a physiochemical change in which the supercoiled plasmid converts to the open circular and linear form. A variety of storage conditions (low pH, high temperature, low ionic strength) can accelerate this process. Therefore, the removal and/or chelation of trace metal ions (with succinic or malic acid, or with chelators containing multiple phosphate ligands, or with chelating agents such as EDTA) from the DNA plasmid solution, from the formulation buffers or from the vials and closures, stabilizes the DNA plasmid from this degradation pathway during storage.

In one embodiment of the invention, the particles formed by the current method are from about 100 nm to about 2000 nm in diameter. The non-ionic block copolymer particle in the presence of the cationic surfactant will have a positive surface charge whereas the polymer particle in the presence of cationic surfactant and DNA should have a surface charge significantly more negative than the polymer particle alone. The exemplified microparticles described in the Example sections range from about 200-600 nm in diameter with a slightly positive zeta potential measurement in the presence of BAK but without addition of the polynucleotide (about 2.5 mV for CRL-1005 and 0.71 mM BAK) and a negative zeta potential when the polynucleotide (at 5 mg/mL) is present (about −46.6 mV for CRL-1005 and 0.71 mM BAK and 5 mg/mL plasmid DNA). While these values are instructive, they are by no way limiting.

The addition of a cationic surfactant changes the configuration or structural integrity of the particle, which in turn increases the ability of the altered structure to better interact with polynucleotide molecules. Therefore, while ranges of surface charge and size measurements of various particles may be instructive, they are not necessarily limiting. One of ordinary skill in the art can adjust concentrations of one type of block copolymer and one type of cationic surfactant to form distinct microparticles, wherein the microparticles are ultimately characterized by an increased ability to associate with a specific population of polynucleotide molecules.

The formulation produced by the methods of the current invention may be aliquoted into a suitable container for storage. Suitable containers include, but are not limited to, glass vials, glass bottles, syringes, sterilizable plastic bags, polyethylene tubes, vials or bottles, and polypropylene tubes, vials or bottles and any other container suitable for manufacturer bulk use or in the preparation of a kit comprising the polynucleotide based medicaments of the invention.

The method of the present invention also relates to mixing a cationic surfactant, a block copolymer, a population of polynucleotide molecules and an amorphous cryoprotectant or a crystalline bulking agent and any combination thereof at a temperature above the cloud point of said block copolymer. The cloud point is dependent upon the block copolymer used in the mixture of the current invention. However, the suitable cloud point can range from about 1° C. to about 20° C. When CRL-1005 is the block copolymer, the temperature at which the mixture of the current invention is mixed can range from about 8° C. to about 35° C.

To this end, the present invention also relates to a polynucleotide based medicament formulation which first comprises a polynucleotide, an adjuvant component comprising a block copolymer, a cationic surfactant and an amorphous cryoprotectant or a crystalline bulking agent, as described within this specification, and secondly comprising a non-ionic surfactant, such as polysorbate-80 or other excipients, including but not limited to excipients known in the art such as glycerol or propylene glycol, or a non-ionic surfactant listed herein.

In a suitable embodiment of this invention, a formulation comprising a polynucleotide, a block copolymer, a cationic surfactant and an amorphous cryoprotectant or a crystalline bulking agent are co-solubilized at a temperature below the cloud point of the block copolymer. The presence of this cryoprotectant or bulking agent provides stability to the polynucleotide formulation during the freeze-drying process and subsequent reconstitution. By "stability," it is meant that average size and size distribution are not affected, i.e. that little or no fusion or aggregation is observed upon reconstitution.

Amorphous cryoprotectants which are suitable for use herein include inter alia, mono, di, or oligosaccharides, polyols, and proteins such as albumin; disaccharides such as sucrose and lactose; monosaccharides such as fructose, galactose and glucose; poly alcohols such as glycerol and sorbitol; and hydrophilic polymers such as polyethylene glycol.

The amorphous cryoprotectant is suitably added to the formulations of the present invention before freezing, in which case it can also serve as a bulking agent. However, as a hydrophilic component, it may also provide for enhanced liquid stability.

With regard to crystalline bulking agents, such agents are often used in the preparation of pharmaceutical compositions to provide the necessary bulk upon lyophilization. Many types of crystalline bulking agents are known in the art. (See, Martini et al., *PDA J. Pharm Sci Tech* 51(2):62-67, 1997). Exemplary crystalline bulking agents include D-mannitol, trehalose, and dextran. As the aforementioned are exemplary only, one skilled in the art would recognize that any compound which, when included in the formulations of the present invention during freezing or lyophilization under given conditions, forms crystals, would be considered a suitable crystalline bulking agent. Within the context of the present invention a crystalline bulking agent is generally defined as a compound which can exist in a crystalline form and whose glass transition point (Tg) is below the temperature at which it is being freeze-dried. For example, a conventional freeze-dryer operates at a shelf-temperature from between about −10° C. to about −50° C. Therefore, in one embodiment, a crystalline bulking agent has a Tg below about −50° C.

In a suitable embodiment, the solution comprises about 1% to about 20% (w/v) of the amorphous cryoprotectant or crystalline bulking agent. In a suitable embodiment, the solution contains about 3% to about 17%, about 5% to about 15% or about 8% to about 12% (w/v) amorphous cryoprotectant or crystalline bulking agent. For example about 8%, about 9%, about 10%, about 11%, or about 12% (w/v) amorphous cryoprotectant or crystalline bulking agent.

Suitable for use in the present invention are cryoprotectants and bulking agents from the group consisting of, but not limited to the following sugars: sucrose, lactose, trehalose, maltose or glucose. In a suitable embodiment, the solution comprises about 1% to about 20% (w/v) sugar. In a suitable embodiment, the solution contains about 3% to about 17%, about 5% to about 15% or about 8% to about 12% (w/v) sugar. For example about 8%, about 9%, about 10%, about 11%, or about 12% (w/v) sugar.

In another suitable embodiment the solution contains about 1% to about 20% (w/v) sucrose. In a suitable embodiment, the solution contains about 3% to about 17%, about 5% to about 15% or about 8% to about 12% (w/v) sucrose. For example about 8%, about 9%, about 10%, about 11%, or about 12% (w/v) sucrose. In yet another suitable embodiment, the solution contains about 10% (w/v) sucrose.

In a suitable embodiment of this invention, a formulation comprising a polynucleotide, a block copolymer, a cationic surfactant, an amorphous cryoprotectant or a crystalline bulking agent and a pH buffering agent are co-solubilized at a temperature below the cloud point of the block copolymer.

In another suitable embodiment, the solution comprising a block copolymer, cationic surfactant, polynucleic acid and amorphous cryoprotectant or crystalline bulking agent also contains a physiologic buffer that maintains the solution pH within the range of about pH 4.0 to about pH 9.0. In a suitable embodiment, the pH of the co-solubilized mixture is about pH 5.0 to about pH 8.0, about pH 6.0 to about pH 8.0, or about pH 7.0 to about pH 7.5. For example, the pH of the co-solubilized mixture is about pH 7.0, about pH 7.1, about pH 7.2, about pH 7.3, about pH 7.4 or about pH 7.5.

pH buffering agents suitable for use in the invention include, but are not limited to, saline, PBS, N-(2-Hydroxyethyl)piperazine-N'-(2-ethanesulfonic acid) (HEPES), 3-(N-Morpholino)propanesulfonic acid (MOPS), 2-bis(2-Hydroxyethyl)amino-2-(hydroxymethyl)-1,3-propanediol (BIS-TRIS), potassium phosphate (KP), sodium phosphate (NaP), dibasic sodium phosphate ($Na_2HPO_4$), monobasic sodium phosphate ($NaH_2PO_4$), monobasic sodium potassium phosphate ($NaKHPO_4$), magnesium phosphate ($Mg_3(PO_4)_2 \cdot 4H_2O$), potassium acetate ($CH_3COOK$), D(+)-α-sodium glycerophosphate ($HOCH_2CH(OH)CH_2OPO_3Na_2$) and other physiologic buffers known to those skilled in the art. Additional pH buffering agents for use in the invention include, a salt M-X dissolved in aqueous solution, association, or dissociation products thereof, where M is an alkali metal (e.g., $Li^+$, $Na^+$, $K^+$, $Rb^+$), suitably sodium or potassium, and where X is an anion selected from the group consisting of phosphate, acetate, bicarbonate, sulfate, pyruvate, and an organic monophosphate ester, preferably glucose 6-phosphate or DL-a-glycerol phosphate. and other physiologic buffers known to those skilled in the art. In a suitable embodiment of the invention, the pH buffering agent is selected from the group consisting of sodium phosphate, potassium phosphate, dibasic sodium phosphate ($Na_2HPO_4$), monobasic sodium phosphate ($NaH_2PO_4$), monobasic sodium potassium phosphate ($NaKHPO_4$), magnesium phosphate ($Mg_3(PO_4)_2 \cdot 4H_2O$), potassium acetate ($CH_3COOK$), and D(+)-α-sodium glycerophosphate ($HOCH_2CH(OH)CH_2OPO_3Na_2$).

In a suitable embodiment of the invention, the concentration of the pH buffering agent is from about 5 mM to about 25 mM. Suitably, a formulation of the present invention may have a final pH buffering agent concentration of about 7 mM to about 20 mM, or about 8 mM to about 15 mM, or about 9 mM to about 12 mM. For example, a formulation of the present invention may have a final pH buffering agent concentration of about 9 mM, about 10 mM, about 11 mM, or about 12 mM. In another suitable embodiment, the concentration of the pH buffering agent is about 10 mM.

In another suitable embodiment of the invention, the concentration of the pH buffering agent selected from sodium phosphate, potassium phosphate, $Na_2HPO_4$, $NaH_2PO_4$, $NaKHPO_4$, $Mg_3(PO_4)_2 \cdot 4H_2O$, and $HOCH_2CH(OH)CH_2OPO_3Na_2$ is from about 5 mM to about 25 mM. Suitably, a formulation of the present invention may have a final concentration of pH buffering agent selected from sodium phosphate, potassium phosphate, $Na_2HPO_4$, $NaH_2PO_4$, $NaKHPO_4$, $Mg_3(PO_4)_2 \cdot 4H_2O$, and $HOCH_2CH(OH)CH_2OPO_3Na_2$ of about 7 mM to about 20 mM, about 8 mM to about 15 mM, or about 9 mM to about 12 mM. For example, a formulation of the present invention may have a final concentration of pH buffering agent selected from sodium phosphate, potassium phosphate, $Na_2HPO_4$, $NaH_2PO_4$, $NaKHPO_4$, $Mg_3(PO_4)_2 \cdot 4H_2O$, and $HOCH_2CH(OH)CH_2OPO_3Na_2$ of about 9 mM, about 10 mM, about 11 mM, or about 12 mM. In another suitable embodiment, the concentration of pH buffering agent selected from sodium phosphate, potassium phosphate, $Na_2HPO_4$, $NaH_2PO_4$, $NaKHPO_4$, $Mg_3(PO_4)_2 \cdot 4H_2O$, and $HOCH_2CH(OH)CH_2OPO_3Na_2$ is about 10 mM. In an alternative embodiment, the concentration of sodium phosphate is about 10 mM.

In one suitable embodiment of the invention, a formulation comprising a polynucleic acid, block copolymer, cationic surfactant, and an amorphous cryoprotectant or crystalline bulking agent, such as 10% (w/v) sucrose, are co-solubilized at a temperature below the cloud point of the block copolymer. This mixture is then lyophilized.

In another suitable embodiment of the invention, a formulation comprising a polynucleic acid, a block copolymer, cationic surfactant, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This mixture is then lyophilized.

In another alternative embodiment, a formulation comprising a polynucleic acid, a block copolymer, cationic surfactant, and an amorphous cryoprotectant or crystalline bulking agent, such as 10% (w/v) sucrose, are co-solubilized at a temperature below the cloud point of the block copolymer. This mixture is then sterilized via cold filtering prior to lyophilization.

In another suitable embodiment, a formulation comprising a polynucleic acid, a block copolymer, cationic surfactant, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This mixture is then sterilized via cold filtering prior to lyophilization.

The cold filtration step must take place at a temperature below the cloud point of the block copolymer comprised in the formulation. The cold filtration step is suitably performed at a temperature between about −2° C. to about 8° C. For example, the cold filtration step can be performed at about −2° C., at about −1° C., at about 0° C., at about 1° C., at about 2° C., at about 3° C., at about 4° C., at about 5° C., at about 6° C., at about 7° C. or at about 8° C.

The filtration of the cold solution (from about −2° C. to about 8° C.) of polynucleotide, block copolymer, and cationic surfactant provides a cost-effective and time-efficient method by which to sterilize the solution. This filtration step eliminates the need to pre-sterilize the polynucleotide, block copolymer and cationic surfactant prior to mixing. By passing the mixture through a sterile filter with a defined pore size smaller than bacterial pathogens, the solution is sterilized. The pore size of the filters utilized in the cold filtration step in the present invention are suitably from about 0.01 microns to about 2 microns. Alternatively, the pore size of the filters utilized in the cold filtration step in the present invention is about 0.05 microns to about 0.25 microns. For example, pore size of the filters for the cold filtration step can be about 0.05 microns, about 0.08 microns, about 0.1 microns, about 0.15 microns, about 0.16 microns, about 0.17 microns, about 0.18 microns, about 0.19 microns, about 0.2 microns, about 0.21 microns, about 0.22 microns, about 0.23 microns, about 0.24 microns, or about 0.25 microns.

In an alternative embodiment of the invention, a formulation comprising a polynucleic acid, block copolymer, cationic surfactant, and an amorphous cryoprotectant or crystalline bulking agent, such as 10% (w/v) sucrose, are co-solubilized at a temperature below the cloud point of the block copolymer. This solution is then cycled through its cloud point temperature several times, prior to being sterilized via cold filtering and subsequent freeze-drying.

In a suitable embodiment of the invention, a formulation comprising a polynucleic acid, block copolymer, cationic surfactant, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This solution is then cycled through its cloud point temperature several times, prior to being sterilized via cold filtering and subsequent freeze-drying.

In another suitable embodiment, a formulation comprising a polynucleic acid, the block copolymer CRL-1005, the cationic surfactant BAK, and an amorphous cryoprotectant or crystalline bulking agent, such as 10% (w/v) sucrose, are co-solubilized at a temperature below the cloud point of the block copolymer. This solution is then lyophilized.

In another suitable embodiment, a formulation comprising a polynucleic acid, the block copolymer CRL-1005, the cationic surfactant BAK, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This solution is then lyophilized.

In another alternative embodiment, a formulation comprising a polynucleic acid, the block copolymer CRL-1005, the cationic surfactant BAK, and an amorphous cryoprotectant or crystalline bulking agent, such as 10% (w/v) sucrose, are co-solubilized at a temperature below the cloud point of the block copolymer. This solution is then sterilized via cold filtering prior to lyophilization.

In another suitable embodiment, a formulation comprising a polynucleic acid, the block copolymer CRL-1005, the cationic surfactant BAK, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This solution is then sterilized via cold filtering prior to lyophilization.

In another embodiment of the invention, a formulation comprises a polynucleic acid, the block copolymer CRL-1005, the cationic surfactant BAK, and an amorphous cryoprotectant or crystalline bulking agent, such as 10% (w/v) sucrose, are co-solubilized at a temperature below the cloud point of the block copolymer. This solution is then cycled through its cloud point temperature several times, prior to being sterilized via cold filtering and subsequent freeze-drying.

In another suitable embodiment of the invention, a formulation comprises a polynucleic acid, the block copolymer CRL-1005, the cationic surfactant BAK, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This solution is then cycled through its cloud point temperature several times, prior to being sterilized via cold filtering and subsequent freeze-drying.

In another embodiment of the invention, a formulation comprises a polynucleic acid, the block copolymer CRL-1005, a cationic surfactant selected from the following group of cationic lipids: Bn-DHxRIE, DHxRIE-OAc, DHxRIE-OBz and Pr-DOctRIE-OAc, and an amorphous cryoprotectant or crystalline bulking agent, such as 10% (w/v) sucrose, are co-solubilized at a temperature below the cloud point of the block copolymer. This solution is then lyophilized.

In another suitable embodiment of the invention, a formulation comprising a polynucleic acid, the block copolymer CRL-1005, a cationic surfactant selected from the following group of cationic lipids: Bn-DHxRIE, DHxRIE-OAc, DHx-RIE-OBz and Pr-DOctRIE-OAc, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This solution is then lyophilized.

In yet another embodiment of the invention, a formulation comprising a polynucleic acid, the block copolymer CRL-1005, a cationic surfactant selected from the following group of cationic lipids: Bn-DHxRIE, DHxRIE-OAc, DHxRIE-OBz and Pr-DOctRIE-OAc, and an amorphous cryoprotectant or crystalline bulking agent, such as 10% (w/v) sucrose, are co-solubilized at a temperature below the cloud point of the block copolymer. This mixture is then sterilized via cold filtering prior to freeze-drying.

In yet another suitable embodiment of the invention, a formulation comprising a polynucleic acid, the block copolymer CRL-1005, a cationic surfactant selected from the following group of cationic lipids: Bn-DHxRIE, DHxRIE-OAc, DhxRIE-OBz and Pr-DOctRIE-OAc, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This mixture is then sterilized via cold filtering prior to freeze-drying.

In yet another embodiment of the invention, a formulation comprising a polynucleic acid, the block copolymer CRL-1005, a cationic surfactant selected from the following group of cationic lipids: Bn-DHxRIE, DHxRIE-OAc, DHxRIE-OBz and Pr-DOctRIE-OAc, and an amorphous cryoprotectant or crystalline bulking agent, such as 10% (w/v) sucrose, are co-solubilized at a temperature below the cloud point of the block copolymer. This solution is then cycled through its cloud point temperature several times, prior to being sterilized via cold filtering and subsequent freeze-drying.

In yet another embodiment of the invention, a formulation comprising a polynucleic acid, the block copolymer CRL-1005, a cationic surfactant selected from the following group of cationic lipids: Bn-DHxRIE, DHxRIE-OAc, DHxRIE-OBz and Pr-DOctRIE-OAc, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This solution is then cycled through its cloud point temperature several times, prior to being sterilized via cold filtering and subsequent freeze-drying.

In another embodiment of the invention, a formulation comprising a polynucleic acid, the block copolymer CRL-1005, the cationic lipid Pr-DOctRIE-OAc, and an amorphous cryoprotectant or crystalline bulking agent, such as 10% (w/v) sucrose, are co-solubilized at a temperature below the cloud point of the block copolymer. This solution is then lyophilized.

In another suitable embodiment of the invention, a formulation comprising a polynucleic acid, the block copolymer CRL-1005, the cationic lipid Pr-DOctRIE-OAc, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This solution is then lyophilized.

In yet another embodiment of the invention, a formulation comprising a polynucleic acid, the block copolymer CRL-1005, the cationic lipid Pr-DOctRIE-OAc, and an amorphous cryoprotectant or crystalline bulking agent, such as 10% (w/v) sucrose, are co-solubilized at a temperature below the cloud point of the block copolymer. This mixture is then sterilized via cold filtering prior to freeze-drying.

In yet another suitable embodiment of the invention, a formulation comprising a polynucleic acid, the block copolymer CRL-1005, the cationic lipid Pr-DOctRIE-OAc, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This mixture is then sterilized via cold filtering prior to freeze-drying.

In yet another embodiment of the invention, a formulation comprising a polynucleic acid, the block copolymer CRL-1005, the cationic lipid Pr-DOctRIE-OAc, and an amorphous cryoprotectant or crystalline bulking agent, such as 10% (w/v) sucrose, are co-solubilized at a temperature below the cloud point of the block copolymer. This solution is then cycled through its cloud point temperature several times, prior to being sterilized via cold filtering and subsequent freeze-drying.

In yet another embodiment of the invention, a formulation comprising a polynucleic acid, the block copolymer CRL-1005, the cationic lipid Pr-DOctRIE-OAc, an amorphous cryoprotectant or crystalline bulking agent, such as 10% (w/v) sucrose, and a suitable pH buffering agent, such as 10 mM sodium phosphate, are co-solubilized at a temperature below the cloud point of the block copolymer. This solution is then cycled through its cloud point temperature several times, prior to being sterilized via cold filtering and subsequent freeze-drying.

These example and equivalents thereof will become more apparent to those skilled in the art in light of the present disclosure and the accompanying claims. It should be understood, however, that the examples are designed for the purpose of illustration only and not limiting of the scope of the invention in any way. All patents and publications cited herein are fully incorporated by reference herein in their entirety.

EXAMPLES

Example 1

Aim: Prepare a DNA/poloxamer/BAK formulation (5 mg/ml DNA, 7.5 mg/mL CRL-1005, 0.3 mM BAK) in 10% sucrose, 10 mM sodium phosphate vehicle and lyophilize the formulation and determine the effect on particle size of the process.

Apparatus: A 15 ml round bottom flask, with a ⅜"×³⁄₁₆" egg-shaped magnetic stirrer bar (Bel-art products) and a corning stirrer/hotplate and an ice bath.

Method: The required volume of DNA (6.1 mg/mL DNA, VR 4700, in 10% sucrose, 10 mM Sodium phosphate), was placed into the 15 mL round bottom flask and the solution stirred with a magnetic stirrer bar, in an ice bath on top of a Corning stirrer/hotplate (speed 4, hotplate off) for 10 minutes. The CRL-1005 was then added using a positive displacement pipette and the solution stirred for a further 30 minutes on ice. The required volume of BAK solution to give a final concentration of 0.3 mM was then added drop wise, slowly, to the stirring solution over 1 minute using a 1 ml pipette. The solution at this point was clear since it was below the cloud point of the poloxamer and was stirred on ice for 30 minutes. The ice bath was then removed and the solution stirred at ambient temperature for 15 minutes to produce a cloudy solution as the poloxamer passed through the cloud point.

The flask was then placed back into the ice bath and stirred for a further 15 minutes to produce a clear solution as the mixture cooled below the cloud point of the CRL-1005. The ice bath was again removed and the solution stirred for a further 15 minutes. Stirring for 15 minutes above and below the cloud point (total of 30 minutes), was defined as one thermal cycle. The mixture was cycled two more times. The solution was then diluted 1:2 with PBS and a 20 μL aliquot of the solution was then removed, diluted in 2 mL of filtered (0.2 μm) PBS and the particle size determined using a Malvern 3000 HS Zetasizer.

The formulation was then filtered sterilized. A 50 mL Steriflip filtration system was placed in an ice bucket, with a vacuum line attached and left for 1 hour to allow the device to equilibrate to the temperature of the ice. The poloxamer formulation was then filtered under vacuum, below the cloud point and then allowed to warm above the cloud point. A 20 μL aliquot of the solution was then removed, diluted in 2 mL of filtered (0.2 μm) PBS and the particle size determined.

Three 5 mL borosilicate vials (Wheaton) were then filled with 1 mL each of the formulation and the vials placed in a computer controlled Virtis Advantage freeze dryer. Initially the vials were cooled below −40° C. for at least two hours and then the condenser was cooled to below −40° C. and the vacuum reduced to below 300 mTorr. The first step in primary drying was to hold the vials at −40° C. for one hour, under a vacuum of 120 mTorr. Then the temperature was raised to 20° C. over eight hours and the vacuum maintained at 120 mTorr. After eight hours the temperature and vacuum were maintained for a further one-hour. The secondary drying step involved raising the temperature to 30° C. over 30 minutes and holding this temperature for a further two hours, while maintaining a vacuum of 120 mTorr. Finally the temperature was reduced to 20° C. over 30 minutes; the vials were sealed with grey butyl rubber stoppers (WestDirect) under vacuum and the samples removed for analysis.

A similar procedure was used to prepare microparticles for lyophilization in PBS. The formulation contained final concentrations of 5 mg/ml DNA, 7.5 mg/mL CRL-1005, 0.3 mM BAK. The lyophilized particles in PBS were compared to the lyophilized particles in the 10% sucrose, 10 mM Sodium phosphate solution. Z average mean particle size and polydispersity were measured using a Malvern 3000 HS Zetasizer for both type of particles before and after lyophilization and the result are shown in Table 1.

TABLE 1

| | Vehicle | Z average mean (nm) | Polydispersity |
|---|---|---|---|
| Before Lyophilization | PBS | 247.2 | 0.04 |
| After Lyophilization | PBS | 268.8 | 0.59 |
| Before Lyophilization | 10% Sucrose 10 mM NaP | 223.9 | 0.07 |
| After Lyophilization | 10% Sucrose 10 mM NaP | 205.4 | 0.10 |

Example 2

One of the lyophilized samples as prepared in the 10% sucrose, 10 mM Sodium phosphate solution as in Example 1 was reconstituted with 960 μl of sterile water for injection and gently mixed by hand and left on the bench top for 15 minutes. A 20 μl aliquot of this solution was then removed at 15, 60, 120, 240, 360 minute intervals, diluted in 2 ml of filtered (0.2 μm) 10% sucrose, 10 mM Sodium phosphate. The Z average mean and polydispersity of the particles in these aliquots were measured using a Malvern 3000 HS Zetasizer as above (FIGS. 1A and 1B).

Example 3

Sterile formulations containing DNA, CRL-1005 and other poloxamers with cationic ionic lipids, including but not limited to, benzalkonium chloride in 8.5% sucrose can be prepared as described herein. The mixture is then lyophilized, and when reconstituted, these formulations may be used in immunogenicity studies. The T-cell responses of animals injected with the formulations described above can be measured by IFN-γ ELISpot assay and antigen-specific antibodies can be measured by ELISA. From the data, biologically active formulations with advantageous physical or pharmaceutical properties and/or formulations with enhanced biological activity can then be identified.

Immunogenicity studies can be conducted using the experimental protocol as described below. Groups of nine, six- to eight-week old BALB/c mice (Harlan-Sprague-Dawley) will receive bilateral (50 μL/leg) intramuscular (rectus femoris) injections of naked plasmid DNA or formulated plasmid DNA. The plasmid (VR4700) to be injected in all mice encodes the influenza nucleoprotein (NP). All mice will be boosted on (approximately) days 21 and 49. Sera will be collected from NP-vaccinated mice after the third (~day 60) vaccination, and NP-specific antibody responses will be measured by ELISA. Two weeks after the last immunization, splenocytes will be harvested from three mice/group/day for three sequential days, and antigen specific T-cell responses will be measured by IFN-γ ELISpot assay.

The NP-specific antibodies produced in response to DNA vaccination will be evaluated by ELISA. Briefly, 96 well Costar hi-binding ½ well ELISA plates are coated with 2

µg/mL of recombinant NP protein (Imgenex, San Diego, Calif.) and blocked with 10% fetal bovine serum (FBS) in PBS. Wells are incubated with serial dilutions of each immune serum, and bound anti-NP antibody is detected by the sequential addition of alkaline phosphatase-labeled goat anti-mouse IgG-Fcγ and the colorimetric substrate, ρ-nitrophenylphosphate. Conversion of the substrate is quantified at 405 nm.

The end-point dilution titer is defined as the reciprocal dilution at which the optical density at 405 nm is greater than twice that measured in wells containing assay buffer alone (i.e., the background value). An average absorbance of eight wells containing assay buffer is used to establish the background value. Wells incubated with a pool of sera from NP DNA-vaccinated mice serve as a positive control.

T-cell responses to the DNA vaccines will be determined by quantifying the number of splenocytes secreting IFN-γ in response to antigen-specific stimulation as measured by IFN-γ ELISpot assay. Splenocyte cultures will be grown in RPMI-1640 medium containing 25 mM HEPES buffer and L-glutamine and supplemented with 10% (v/v) FBS, 55 µM β-mercaptoethanol, 100 U/mL of penicillin G sodium salt, and 100 µg/mL of streptomycin sulfate. ImmunoSpot plates (Cellular Technology Limited, Cleveland, Ohio) are coated with rat anti-mouse IFN-γ monoclonal antibody (BD Biosciences, San Diego, Calif.), and blocked with RPMI-1640 medium. Splenocyte suspensions can be produced from individual vaccinated mice and seeded in ELISpot plates at $1 \times 10^6$, $3 \times 10^5$, or $1 \times 10^5$ cells/well in RPMI medium containing 1 µg/mL of the appropriate MHC class I-restricted peptide (M84, $^{297}$AYAGLFTPL$^{305}$, Imgenex, San Diego, Calif.; NP, $^{147}$TYQRTRALV$^{155}$, Sigma/Genosys, The Woods, Tex.) or 20 µg/mL of protein antigen with (CD8+ T cell ELISpot assay) or without (CD4+ T cell ELISpot assay) 1 U/mL of recombinant murine IL-2 (Roche, Indianapolis, Ind.). Control wells contain $1 \times 10^6$ splenocytes incubated in medium with or without IL-2 only (no antigen). After a 20-hour incubation at 37° C., captured IFN-γ is detected by the sequential addition of biotin-labeled rat anti-mouse IFN-γ monoclonal antibody and avidin-horseradish peroxidase. Spots produced by the conversion of the colorimetric substrate, 3-amino-9-ethylcarbazole (AEC), are quantified by an ImmunoSpot reader (Cellular Technology Limited, Cleveland, Ohio).

What is claimed is:

1. A method of preparing a lyophilized composition comprising:
   (a) mixing
   (i) polyoxyethylene (POE) and polyoxypropylene (POP) blockcopolymer;
   (ii) a polynucleotide;
   (iii) a cationic surfactant selected from the group consisting of benzalkonium chloride (BAK), benethonium chloride, cetrimide, cetylpyridinium chloride, acetyl triethylammonium chloride, (±)-N-(Benzyl)-N,N dimethyl-2,3-bis(hexyloxy)-1-propanaminium bromide (Bn-DHxRIE), (±)-N-(2 Acetoxyethyl)-N,N-dimethyl-2,3-bis(hexyloxy)-1-propanaminium bromide (DHxRIE-OAc), (±)-N-(2-Benzoyloxyethyl)-N,N-dimethyl-2,3-bis(hexyloxy)-1 propanaminium bromide (DHxRIE-OBz) and (±)-N-(3-Acetoxypropyl)-N,N dimethyl-2,3-bis(octyloxy)-1-propanaminium chloride (Pr-DOctRIE-OAc); and
   (iv) a compound selected from the group consisting of monosaccharides, disaccharides, oligosaccharides, sorbitol, hydrophilic polymers, proteins and any combination thereof;
   at a temperature below the cloud point of said block copolymer to form a mixture; and
   (b) cold filtering the mixture, wherein filtration occurs at a temperature below the cloud point of the block copolymer; and
   (c) lyophilizing the mixture;
   wherein the lyophilized mixture form a stable, mono-dispersed composition upon reconstitution with an aqueous solution.

2. The method of claim 1, wherein said block copolymer is of the general formula: HO(C2H4O)x(C3H6O)y(C2H4O)xH; wherein (y) represents a number such that the molecular weight of the hydrophobic POP portion (C3H6O) is up to approximately 20,000 daltons and wherein (x) represents a number such that the percentage of the hydrophilic POE portion (C2H4O) is between approximately 1% and 50% by weight.

3. The method of claim 1, wherein said block copolymer is of the general formula: HO(C3H6O)y(C2H4O)x(C3H6O)yH; wherein (y) represents a number such that the molecular weight of the hydrophobic POP portion (C3H6O) is up to approximately 20,000 daltons and wherein (x) represents a number such that the percentage of the hydrophilic POE portion (C2H4O) is between approximately 1% and 50% by weight.

4. The method of claim 1, wherein said mixing step (a) is performed at a temperature of about −2° C. to about 8° C.

5. The method of claim 1, wherein said cold filtration step is performed at a temperature of about −2° C. to about 8° C.

6. The method of claim 1, wherein said cold filtration step is performed using a filter with a pore size of about 0.01 microns to about 2 microns.

7. The method of claim 2, wherein said block copolymer is CRL-1005.

8. The method of claim 1, wherein said compound is sucrose.

9. The method of claim 1, wherein said mixture comprises about 1% to about 20% (w/v) of said compound.

10. The method of claim 8, wherein the final concentration of sucrose is about 10% (w/v).

11. The method of claim 1, wherein said mixture additionally comprises a pH stabilizing physiologic buffer.

12. The method of claim 11, wherein said physiologic buffer is selected from the group consisting of: saline, PBS, HEPES, MOPS, BIS-TRIS, sodium phosphate, potassium phosphate, dibasic sodium phosphate (Na2HPO4), monobasic sodium phosphate (NaH2PO4), monobasic sodium potassium phosphate (NaKHPO4), magnesium phosphate (Mg3(PO4)2.4H2O), or D(+)-□-sodium glycerophosphate (HOCH2CH(OH)CH2OPO3Na2).

13. The method of claim 12, wherein said physiologic buffer is sodium phosphate.

14. The method of claim 11, wherein the concentration of said physiologic buffer in the mixture is from about 5 mM to about 25 mM.

15. The method of claim 13, wherein said sodium phosphate is at a concentration of about 5 mM to about 25 mM.

16. The method of claim 1, wherein the final concentration of said cationic surfactant present in said mixture is from about 0.01 mM to about 5 mM.

17. The method of claim 1, wherein the final concentration of said block copolymer present in said mixture is from about 1 mg/mL to about 50 mg/mL.

18. The method of claim 1, wherein the final concentration of said polynucleotide molecules present in said mixture is from about 1 ng/mL to about 10 mg/mL.

19. The method of claim 1, wherein said cationic surfactant is benethonium chloride.

20. The method of claim 1, wherein said cationic surfactant is cetrimide.

21. The method of claim 1, wherein said cationic surfactant is cetylpyridinium chloride.

22. The method of claim 1, wherein the cationic surfactant is acetyl triethylainmonium chloride.

23. The method of claim 1, wherein said cationic surfactant is (±)-N-(Benzyl)-N,N dimethyl-2,3-bis(hexyloxy)-1-propanaminium bromide (Bn-DHxRIE).

24. The method of claim 1, wherein said cationic surfactant is (±)-N-(2 Acetoxyethyl)-N,N-dimethyl-2,3-bis(hexyloxy)-1-propanaminium bromide (DHxRIE-OAc).

25. The method of claim 1, wherein said cationic surfactant is (±)-N-(2-Benzoyloxyethyl)-N,N-dimethyl-2,3-bis(hexyloxy)-1 propanaminium bromide (DHxRIE-OBz).

26. The method of claim 1, wherein said cationic surfactant is (±)-N-(3-Acetoxypropyl)-N,N dimethyl-2,3-bis(octyloxy)-1-propanaminium bromide (Pr-DOctRIE-OAc).

27. The method of claim 1, wherein said compound is one or more monosaccharides.

28. The method of claim 1, wherein said compound is one or more disaccharides.

29. The method of claim 1, wherein said compound is one or more oligosaccharides.

* * * * *